United States Patent [19]

Muyskens et al.

[11] Patent Number: 5,157,963

[45] Date of Patent: Oct. 27, 1992

[54] PROCEDURE FOR QUALIFYING SYNTHETIC BASE GEAR LUBRICANT

[75] Inventors: Dale E. Muyskens, Vicksburg; James E. Newkirk, Paw Paw, both of Mich.

[73] Assignee: Eaton Corporation, Cleveland, Ohio

[21] Appl. No.: 526,823

[22] Filed: May 22, 1990

[51] Int. Cl.$^5$ ............................................. G01M 13/02
[52] U.S. Cl. ................................................. 73/53.05
[58] Field of Search ..................... 73/10, 61.2, 64, 64.1

[56] References Cited

U.S. PATENT DOCUMENTS 4,007,629  2/1977  Hochstein ............................... 73/64

OTHER PUBLICATIONS

"Automotive Gear Lubrication: an Overview", Aug. 1985, vol. 93, No. 8, pp. 60-67.

*Primary Examiner*—Jerry W. Myracle
*Attorney, Agent, or Firm*—P. S. Rulon; L. E. Cargill

[57] ABSTRACT

A procedure for qualifying a proposed synthetic lubricant includes: (1) compatibility testing the proposed lubricant with previously approved synthetic lubricants; (2) stability testing the lubricant for thermal oxidation by testing the lubricant in a heated gear box; (3) corrosion testing the proposed lubricant by a copper strip tarnish test; (4) field testing the proposed lubricant to evaluate the ability of the lubricant to withstand extended drain intervals while still performing its function; and analyzing all of the results of those tests. In another embodiment, the lubricant furthermore undergoes a seal life test to evaluate the appearance of various covers and seals for degradation due to long term exposure to the lubricant.

29 Claims, 3 Drawing Sheets

PROCEDURE FOR QUALIFYING SYNTHETIC BASE GEAR LUBRICANT

TECHNICAL FIELD

This invention relates to a testing procedure for gear lubricants, and more particularly relates to a procedure for qualifying synthetic gear lubricants.

BACKGROUND OF THE INVENTION

Proper lubrication is important to long gear life, especially in vehicle transmissions. Maintaining a proper oil level with the correct grade and type of oil is key to the extended life of gears and bearings in transmissions. Down times for changing of the oil and maintenance of the transmission contributes to truck down time, and is a major consideration for truck fleets as well as the individual owner operators. It has long been desired in the truck industry to have extended oil change intervals, which reduces down time due to maintenance.

In the past, transmission manufacturers of heavy duty trucks have recommended oil change intervals of 50,000 miles in heavy duty applications with petroleum based lubricants. With today's synthetic lubricants, these manufacturers have been able to extend those change intervals approximately five times, recommending change intervals of 250,000 miles after the original factory oil fill is drained and refilled with the synthetic lubricants at 5,000 miles or less. When the original factory fill is the new synthetic lubricant, no initial change is required. Several manufacturers are currently offering extended warranties for failure mode at 750,000 miles.

Until recently, petroleum based oils were used for lubrication in heavy duty truck transmissions even though they were susceptible to oxidation when operating the transmissions at oil sump temperatures above 230° F. Many of the mineral gear oils break down above 230° F. and oxidize, and thereby deposit carbonaceous coatings onto seals, bearings and gears that may cause premature failures. Consequently, regular oil changes were required in order to minimize oxidation and these deposits, to assure maximum component life and to maintain the warranties with the transmission manufacturers. The lower temperature limit and requirements for a transmission oil cooler restricted the success of the mineral gear oils to milder applications.

The new synthetic lubricants which are currently available can be operated at temperatures up to 250° F., with intermittent operating temperatures up to 300° F., without harming the transmission. If the average operating temperature is above about 250° F., the transmission may require more frequent oil changes or external cooling. The following conditions, in any combination, can cause operating temperatures of over 250° F. (1) operating consistently at slow speeds; (2) high ambient temperatures; (3) restricted air flow around the transmission; (4) having the exhaust system too close to the transmission; and (5) high horse power, over-drive operation.

Because many manufacturers design their transmissions so that the internal parts operate in a free flowing bath of oil which is circulated by the motion of gears and shafts, the oil droplet surface area is highly increased during operation, thereby rendering it particularly susceptible to oxidation. This oxidation helps to cause the accumulation of carbon deposits on the oil seal, which deteriorates the sealing material. It has long been established that there is a notable difference in seal life when using different lubricants. Once the seal material has deteriorated, the surfaces which mate to the seal may also be damaged or destroyed. These material failures cause the loss of lubricant over time, with an end result of low lubricant levels, and subsequent transmission failures. Fleet records have shown a failure rate of about 1 seal every 150,000 miles (on an average) during a normal maintenance period in a heavy duty truck transmission using mineral oil or petroleum based lubricants. The new synthetic lubricants have shown no evidence of leakage or recorded failure during the same maintenance in trucks, which indicate an extended seal life significantly beyond the capability of normal petroleum based lubricants.

Therefore, because petroleum based lubricants oxidize under the high operating temperatures to which transmissions are now being subjected, the oxidation problem we now experience causes deposits to form within the transmission, leaving a crusty carbon film throughout the transmission. These deposits adhere to bearings, gear hubs, tooth surfaces, sliding clutches, synchronizers and all other internal parts. High acid levels which develop during operation encourage this oxidation. Therefore, it is advisable to qualify various lubricants which will operate at higher temperatures with a lower rate of oxidation, lubricants which will experience lower acid levels, thereby encouraging less oxidation. Synthetic lubricants do not include the residual sulfur component that petroleum based lubricants generally do, and an approved synthetic lubricant will generally allow for extended drain intervals which gives the added benefit of reduced down time, and cleaner operating transmissions which give longer life.

In addition, the thermal aspects of today's truck design indicate that transmissions now operate at higher critical temperatures, requiring lubricants to perform under higher thermal conditions. Through research and testing, it has been determined that most petroleum based lubricants manufactured today have a lower thermal stability than those which are required during the high temperature operations needed by recent trucks. Due to the higher temperatures, and, as discussed hereinabove, the concomitant deposition of carbonaceous sludge and varnish and other accumulation of debris can become a factor in heat concentration, which possibly contributes to synchronizer failure, and ultimate transmission failure. Internal debris and deposits pose problems during transmission operation. Accumulation may lead to premature failure of the entire transmission unit. The extent of actual effect during operation may depend upon extremely careful maintenance, but the possible result is shortened transmission life due to excessive oxidation deposits.

In an attempt to overcome these thermal problems, new synthetic lubricants are being manufactured with thermally stable additive packages which are currently available from suppliers. Truck component manufacturers are encouraging oil suppliers to produce thermally stable additive packages for the synthetic lubricants which are more appropriate for today's truck designs which require higher temperature operating conditions. These suppliers of thermally stable additives blend the additives packages into synthetic base stock lubricants. The blended packages outperform other lubricants in the transmission because they are not only thermally stable, but the synthetic base stock does not generally thicken over time, allowing the longer drain intervals between oil changes.

Therefore, it has become apparent to transmission manufacturers that the generation of a procurement specification for qualifying lubricants has become imperative.

The old methods for testing lubricants included the ASTM designation D-130 standard test for detection of copper corrosion from petroleum products by the "Copper Strip Tarnish Test". This standard test was issued under the fixed designation D-130-80. The number immediately following the designation indicates the year of original adoption or, in the case of revision, the year of last revision. This is also a standard test of the Institute of Petroleum issued under their fixed designation IP 154. This method has also been adopted for use by government agencies to replace method 5325 of Federal Test Methods Standard No. 791B.

This method covers the detection of the corrosiveness to copper of various gasolines, fuel oils, cleaners and solvents, distillate fuel oils and lubricants. The test basically consists of placing a specially prepared copper strip blank in a copper strip corrosion test bomb constructed of stainless steel and capable of withstanding test pressures and temperatures. The lubricant is maintained in a liquid bath at a predescribed temperature, generally about 100° C. for lubricant oils, and held at that temperature for about 3 hours. The copper strip is immersed in the heated lubricant oil and thereafter evaluated for copper strip applications. It is desirable to achieve classification 1-A, which exhibits a slight tarnish, light orange in color, almost the same as a freshly polished strip. The copper strip classifications are generally as follows:

TABLE 1

ASTM D 130
Copper Strip Classifications

| Classification | Designation | | Description[4] |
|---|---|---|---|
| Freshly polished strip | — | B | |
| 1 | slight tarnish | a. | Light orange, almost the same as freshly polished strip |
| | | b. | Dark orange |
| 2 | moderate tarnish | a. | Claret red |
| | — | b. | Lavender |
| | — | c. | Multicolored with lavender blue or silver, or both, overlaid on claret red |
| | — | d. | Silvery |
| | — | e. | Brassy or gold |
| 3 | dark tarnish | a. | Magenta overcast on brassy strip |
| | — | b. | Multicolored with red and green showing (peacock), but no gray |
| 4 | corrosion | a. | Transparent black, dark gray or brown with peacock green barely showing |
| | — | b. | Graphite or lusterless black |
| | — | c. | Glossy or jet black |

[4]The ASTM Copper Strip Corrosion Standard is a colored reproduction of strips characteristic of these descriptions.
[B]The freshly polished strip is included in the series only as an indication of the appearance of a properly polished strip before a test run; it is not possible to duplicate this appearance after a test even with a completely noncorrosive sample.

In general, lubricants are subjected to ASTM D-130, in order to test for the corrosiveness on the copper. The interpretation of the corrosiveness of the sample is according to the appearance of the test strip as it agrees with one of the standard strips of the ASTM Copper Strip Corrosion Standards. Should a strip appear to have a darker orange color than standard strip 1-B, the sample is considered as still belonging in classification 1. However, if any evidence of red color is observed, the observed strip belongs in classification 2.

In addition to ASTM D-130, another widely accepted test, the thermal oxidation stability test (TOST), test is performed on a lubricant in a heated gear box. L-60 is currently being approved as a standard lubricant testing method by ASTM. The proposed lubricant is tested within a heated gear box containing two spur gears and a test bearing while operating at a predetermined load with copper strip blanks within the gear box, maintained at about 325° F. while bubbling air at the rate of about 0.3 gallons per hour therethrough for approximately 50 hours of continuous operation. Test results are interpreted by checking weight loss of the copper strip blank, as well as checking the color changes of the front face of the catalyst strip and the gear components and bearings of the heated gear box.

While this performance test has been very helpful in the past in evaluating the appropriateness of various lubricants for transmissions, today's higher thermal operating conditions have necessitated the use of testing the synthetic lubricants which are not readily evaluated by the traditional D-130 and L-60 test as they were generated for petroleum based lubricants.

Therefore, it is an object of this invention to provide a procedure for qualifying new synthetic gear lubricants for use in transmission cases manufactured for today's trucks with extended drain intervals.

SUMMARY OF THE INVENTION

Therefore, in accordance with that object, the present invention discloses a method for qualifying a proposed synthetic gear lubricant which includes additional test methods and steps which go beyond the traditional copper test tarnish test and thermal oxidation stability test which was previously used for petroleum based lubricants for transmissions with a recommended 50,000 mile interval oil change.

In accordance with the present invention, there is disclosed a method which includes testing the lubricant for compatibility with previously approved synthetic lubricants by heating the proposed lubricant with an approved lubricant in each of the following five proportions 90/10, 75/25, 50/50, 25/75, and 10/90 by weight at 0° F., 70° F. and 150° F., respectively, for about 30 days with substantially no haze or separation; testing the lubricant for thermal oxidation stability as described above; testing the lubricant for corrosion resistance by a copper strip tarnish test, as described above; field testing the lubricant in about 100 new, substantially identical vehicles run in on-highway service for at least 275,000 miles, without lubricant change, by inspecting the transmission parts, including the internal transmission case, the shift bar housing, and the rear of the internal case to check for clean appearance, as well as to evaluate gear and transmission component stress and damage and the amount and color of the varnish and sludge deposits existing in the transmission case. Furthermore, the present invention discloses a test for extended seal life by testing at least 50 new, substantially identical vehicles which have been run using the proposed lubricant in on-highway service for at least 300.000 miles without changing the lubricant and evaluating the appearance of the rear bearing covers and seals for general appearance, cleanliness, signs of wearing or degradation of the seal or any surfaces which mate to the seal, and also for the amount and color of the varnish and sludge deposits on the rear bearing cover seal.

Therefore, the prior art methods L-60 and D-130 were not sufficient for evaluating the new synthetic gear lubricants. Traditional bench qualification tests cannot duplicate the performance data obtained in actual service tests, and are therefore inadequate to judge differences in lubricants. Actual field tests are currently the only reliable method to quantify a lubricant's performance comparison. The extension of the L-60 test to 300 hours and the addition of the compatibility test, the field test, and the seal life test as disclosed herein provides a good procedure for evaluating the appropriateness of a proposed synthetic gear lubricant for use in transmissions which have been warranted for extended lifetimes of about 750,000 miles.

The combination of these tests which generally constitute the procurement specification of this invention, has become known as PS-081.

The compatibility test portion of PS-081 procurement specification is important because it has been recognized that truck operators may require some maintenance in a remote location which would not be able to provide the same approved synthetic gear lubricant in order to maintain the warranty and the extended drain interval. Therefore, if the truck driver is on the road and is in a location where he was not able to get the same approved synthetic gear lubricant, it would be important that the approved synthetic lubricant which he may able to procure at that site would be compatible with the synthetic gear lubricant which would be residual in the transmission. Therefore, it is important for a proposed synthetic gear lubricant to be evaluated for compatibility with previously approved lubricants showing substantially no haze or separation, or any other indication of chemical reaction or production of water.

The field test portion of PS-081 is important because an in situ test under actual road conditions is needed to evaluate levels of carbon deposits in the form of varnish and sludge, in order to be able to recommend the synthetic lubricant for use when offering extended life warranties and extended drain intervals for the transmission. Traditional bench qualification tests cannot adequately qualify a new, proposed synthetic lubricant.

Likewise, the seal life test is equally important and is performed on at least 50 trucks that have achieved at least 300,000 miles on-highway service. This test is discussed in greater detail below.

BRIEF DESCRIPTION OF THE DRAWINGS

FIGS. 2a through 2c show rear bearing covers with seals using the same respective lubricants, while

DETAILED DESCRIPTION OF THE INVENTION

Figure 1A:
FIGS. 1a through 1i shows internal parts representative of transmissions which have logged more than 500,000 miles of service with (i) an approved synthetic lubricant, (ii) 50 weight motor oil and (iii) a petroleum based gear lubricant, respectively.
Figure 1D:
Figure 1G:
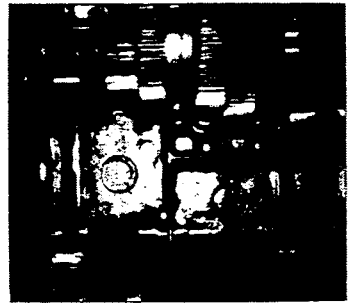
Figure 1B:
Figure 1E:
Figure 1H:
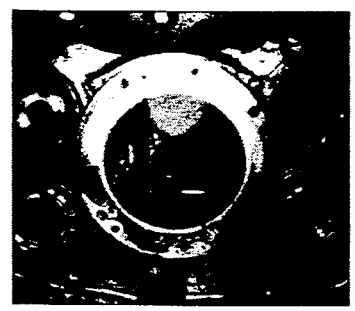
Figure 1C:
Figure 1F:
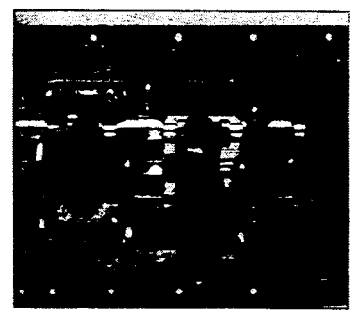
Figure 1I:

The procedure for qualifying a proposed synthetic gear lubricant in accordance with the present invention basically includes the at least some of the following steps:

(1) Compatibility testing for use with other approved synthetic lubricants;

(2) Extended stability testing for thermal oxidation in a laboratory heated gear box;

(3) Corrosion testing the proposed lubricant by a Copper Strip Tarnish Test; and (4) Field testing the proposed lubricant to evaluate (a) the amount and color of varnish and sludge deposits within a transmission case, and (b) gear and transmission component stress and damage.

Furthermore, we may also add the following embodiment:

(5) Performing a seal life test on the transmission cases which have been run in on-highway service to evaluate the appearance of the rear bearing covers and seals for general appearance cleanliness, signs of wearing or degradation of the seal or any surface which mates to the seal, and the amount and color of the carbonaceous varnish and sludge deposits on the rear bearing cover seals.

Each one of these aspects of the procedure for qualifying a proposed synthetic gear lubricant will be addressed individually, although they should be performed as a collective in order to actually qualify a proposed synthetic gear lubricant for use by manufacturers giving extended life warranties. These tests enable a manufacturer to suggest and recommend synthetic gear lubricants for refilling the transmission case in order to effect proper maintenance so that the warranties may be administered.

Generally, the first part of the test to be performed is the compatibility test. Although it is not necessary to perform this test first, it is generally preferred to do so. The synthetic base lubricant should be an SAE grade (J306-C) 50 lubricant and should be compatible with previously approved synthetic lubricants. Compatibility testing shall be performed with at least five proportions of the proposed to previously approved synthetic lubricants including 90/10, 75/25, 50/50, 25/75, and 10/90, each at three temperatures 0° F., 70° F. and 150° F., respectively, for a duration of about 30 days, and evaluation thereafter following. If there is no evidence of haze or separation between the two mixed lubricants, the proposed synthetic based gear lubricant passes the test.

Secondly, the proposed lubricant must endure our modified ASTM L-60 thermal oxidation stability test which has been extended to 300 hours to more closely simulate extreme actual transmission on-road operations. In order for approval, the lubricant must exhibit no more than a viscosity increase of 100%, and gear appearance after the test must be clean. In the standard L-60 test, which is currently being approved by ASTM as a standard method for testing lubricants, a sample of gear lubricant to be tested is placed in a heated test gear box in which two spur gears and a test bearing which is operated at a predetermined load in the presence of a copper catalyst. The copper catalyst is in the form of a copper strip blank similar to that of the D-130 test described below. The temperature of the test lubricant is maintained at about 325° F., while bubbling air at the rate of about 0.3 9 gallons per hour through the lubricant. Our modified L-60 test calls for about 300 hours of continuous operation. This modified test method gives a test procedure for determining the deterioration of gear lubricants when subjected to severe thermal oxidation.

After the L-60 test has been completed, the gear box is torn down and the various components are evaluated. The copper strip blanks are analyzed the same way as with test D-130 described hereinbelow. The gears are evaluated for the amount of (1) sludge (which is the rubbable deposited material) for color ranging from brown to black, and (2) the varnish or lacquer (which is not capable of being rubbed off), also evaluated for color from brown to black. Generally, the deposits must be described for (1) color (from light brown to black); (2) hardness (from very soft to very hard); (3) thickness (as estimated in 1,000th of an inch); and (4) as to type (lacquer or varnish, which cannot be wiped off, or sludge, which is easily removed). In addition, the viscosity increase is also evaluated, as well as the total acid number and n-pentane and toluene insoluble levels. The catalyst weight loss or the copper strip blank is also measured.

The third portion of the test is the detection of copper corrosion by the copper strip tarnish strip, known as D-130. As described above, in the background of the invention, D-130 involves immersing a copper strip blank (which has been carefully polished) in a test bomb with heated lubricants at about 250° F. for a duration of about 3 hours. The proposed lubricant must achieve a 1-A classification, or must be light orange with a slight tarnish, in order to pass this portion of the test. The standard D-130 test requires a lower temperature, that of about 212° F., while our test requires the elevated temperature of 250° F. because our synthetic gear lubricant utilized for the extended warranty must be able to withstand higher temperatures than the traditionally lower temperatures tested for.

The fourth part of the qualifying procedure is the field test which must include fleet on-highway service and must be capable of withstanding extended drain intervals of at least 250,000 miles to qualify the lubricant. This test describes a test procedure for evaluation of the ability of a gear lubricant to withstand extended drain or change intervals of 250,000 miles. The test units must be virtually new transmissions (0-500 miles) and all of the test transmissions must be installed in substantially identically constructed vehicles. The vehicle test specifications shall be as follows: engines 290–400 horse power; weight 55,000-80,000GCW; cab configuration—conventional, or cab over; application —on-highway; and transmission—11600 series and above —overdrive, range box type without oil coolers. The test preferably includes about 100 units in two or more fleets, each transmission accumulating at least 275,000 miles. The number of units and mileage goal were selected to statistically indicate a realistic and reasonable reliability and confidence level for the product. The units are to be run without transmission lubricant changes.

In order to evaluate the results of the field test, we refer now to FIGS. 1a through 2c. The proposed synthetic gear lubricant was run in this transmission more than 500,000 miles of service with proper maintenance. Notice the internal case of FIG. 1a, the rear of the case in FIG. 1b, and the shift bar housing of FIG. 1c and their appearance. Compare those figures to FIGS. 1d through 1f which utilized 50 weight motor oil under the same test conditions. Notice the black deposits shown with the 50 weight motor oil example, compared to the clean appearance of the synthetic gear lubricant utilized in FIGS. 1a through 1c. Furthermore, a petroleum based gear lubricant was utilized in the transmissions shown in FIGS. 1g through 1i. As can be seen by the figures, the synthetic gear lubricant maintained a much cleaner appearance. Usually, cleaner operating conditions relate to better performance, less transmission failure and less maintenance time.

Figure 2A:
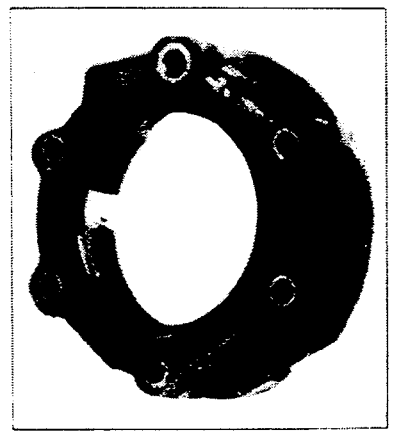
Figure 2B:
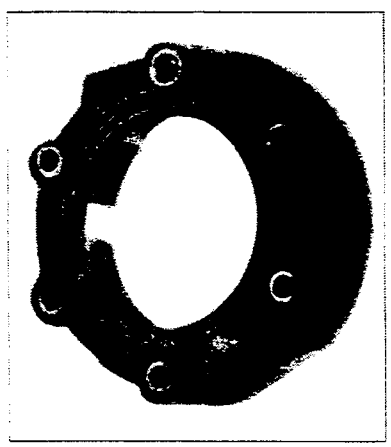
Figure 2C:
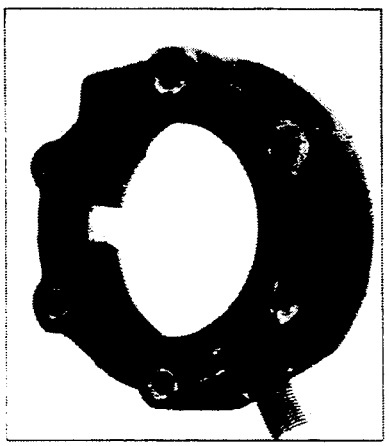
Figure 2D:
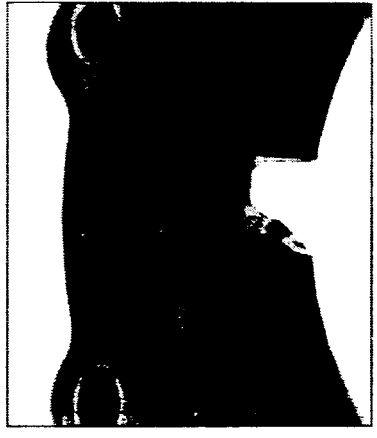
FIGS. 2d through 2f show close-up pictures of the rear bearing cover seals with the use of the various lubricants.
Figure 2E:
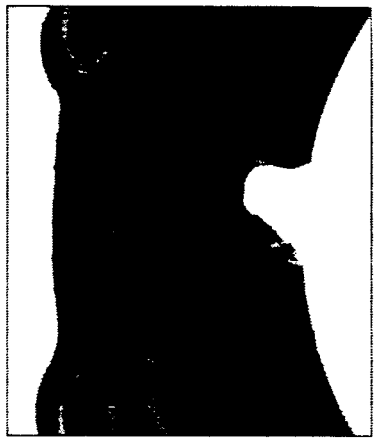
Figure 2F:
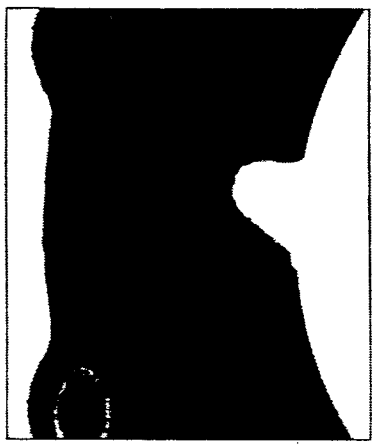

Referring now to FIGS. 2a through 2c, again, the same lubricants were used as in FIG. 1 and the rear bearing covers with seals are shown compared in FIGS. 2a through 2c. Note the generally cleaner appearance of the bearing cover in 2a as compared to the bearing covers in 2b and 2c. Closer photographs are shown in FIGS. 2d through 2f, illustrating the deposition of carbonaceous deposits including varnish and sludge on the seals. As described above, the seals should not have any deposits in order to achieve long life.

Figure 3A:
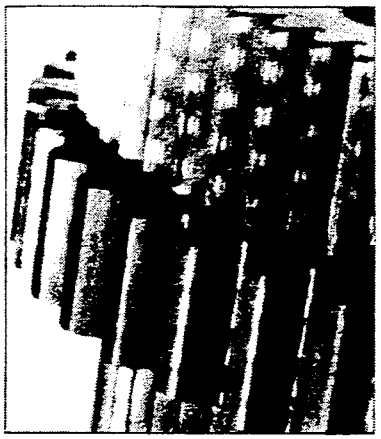
FIGS. 3a through 3c show internal lubricant deposits on front countershafts using the three lubricants.
Figure 3B:
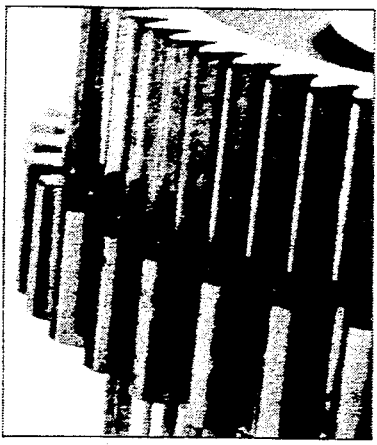
Figure 3C:

In accordance with the field test, FIGS. 3a through 3c show the front countershaft of the transmission after the test has been performed with the above-mentioned three lubricants. Notice the lack of carbon deposition on the front countershaft of the transmission which utilized the qualifying synthetic gear lubricant, while the carbon deposition was thick and black with the other lubricants.

Figure 4A:
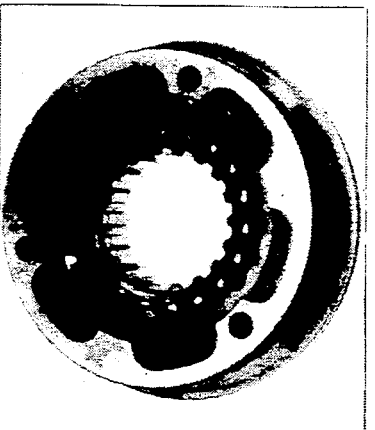
FIGS. 4a through 4c show auxiliary synchronizers after using the three various lubricants.
Figure 4B:
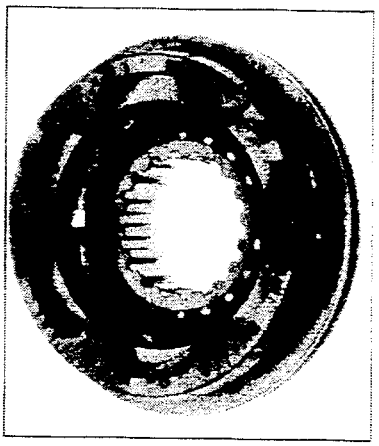
Figure 4C:
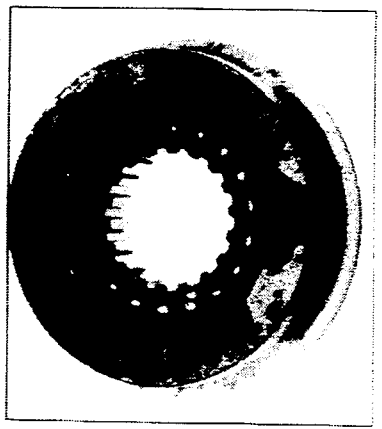

FIGS. 4a through 4c show the auxiliary synchronizers of the three transmissions which were tested with the three lubricants. As can be seen from FIG. 4a, the synthetic gear lubricant shows a very clean appearance with very slight carbonaceous deposits. The other lubricants show greater degrees of deposition and general dirty appearance.

As can be seen from the figures, the general overall appearance of a qualifying synthetic gear lubricant is very clean, and shows very little varnish and sludge. Furthermore, gear and synchronizer wear is evaluated for severity. In order to pass the field test portion of the qualifying procedure, there should be essentially no evidence of wear, and very little evidence of varnish and sludge. Although the basic mineral based oil does not cause varnish and sludge by itself, the additive packages which are included to enhance the performance of the lubricant have a high sulfur phosphorus mix, which causes varnish and sludge. By itself, mineral base oil will only exhibit a problem when the viscosity increases, but generally it will not form varnish or sludge. However, the mineral base oil and the performance additives generally have free bonding sites on the hydrocarbon chains and oxidation occurs at those sites because the lubricant is splashed around when it is used to bathe the gears in operation. With synthetics, all of the bonds are saturated on the hydrocarbon chain, leaving essentially no bonding sites for oxidation to take place. It is the combination of oxidation and sulfur compounds which produce the varnish and sludge as seen in the Figures.

Further in order to evaluate the test results, the viscosity increase of the lubricant used during the test is also measured, along with the total acidity of the lubricant and the n-pentane and toluene components. It goes without saying that the less sludge, varnish, viscosity increase, total acidity and n-pentane and toluene component concentration there is in the system, the more agreeable the lubricant is as a qualifying lubricant.

The final portion of the PS-081 qualifying test for proposed synthetic gear lubricants of the present invention includes an extended seal life test for evaluating the effect of a proposed lubricant on seal life after the seal has been in contact with the proposed synthetic gear lubricant for a minimum of 300,000 miles in preferably at least 50 trucks. A visual analysis is performed which includes an external inspection to determine if seal leakage has begun, and is to be conducted at 50,000 mile intervals. In-depth seal analysis is to be conducted at the end of the test. The seal life test for proposed lubricants can be incorporated into the field test for extended drain intervals as described hereinabove. To evaluate the test results, the first indicator is to review the appearance of the seal and to check for the amount of varnish and sludge which has been deposited. In order to pass this portion of the test, there must not be any significant black carbonaceous deposits on the seal, and there should be a clean appearance. Furthermore, there shall be no varnish build-up, no contamination of the seal material, and essentially no evidence of wearing or degradation of the seal or any surfaces which mate to the seal. This can be seen in FIGS. 2a through 2f and 4a through 4c. If the seal shows no deposits, by meeting these criteria, then the lubricant has passed the seal life test.

If the proposed synthetic gear lubricant passes at least the first four of these tests, and preferably all five of these tests, then the lubricant may qualify for recommendation for use with transmissions having extended warranties. These lubricants may be recommended for extended drain intervals, and shall be approved for extended drain intervals.

While our invention has been described in terms of a few specific examples and configurations, it will be appreciated that other forms could readily be adapted by one skilled in the art. Accordingly, the scope of our invention is to be considered limited only by the following claims.

What is claimed:

1. A procedure for qualifying a proposed synthetic gear lubricant to be used in transmissions having a rear bearing cover and a rear bearing cover seal, comprising:
    testing the lubricant for compatibility with previously approved synthetic lubricants;
    testing the lubricant for thermal oxidation stability by testing the lubricant in a heated test gear box;
    testing the lubricant for corrosion resistance by a copper strip tarnish test; and
    field testing the proposed gear lubricant to evaluate the ability of the lubricant to withstand extended drain intervals while still performing as functioned.

2. The procedure of claim 1, wherein said testing for compatibility includes heating the proposed synthetic lubricant with an approved lubricant in weight percentage ratios of 90/10, 75/25, 50/50, 25/75, and 10/90, respectively.

3. The procedure of claim 2, wherein said heating is accomplished with each weight percentage ratio at 0° F., 70° F., and 150° F.

4. The procedure of claim 1, wherein said testing the lubricant for compatibility is accomplished by blending the proposed lubricant with the previously approved synthetic lubricants for about 430 days in order to evaluate for haze or separation.

5. The procedure of claim 1, wherein said testing for thermal oxidation stability by testing the lubricant in a heated test gear box is accomplished by using a heated test gear box which contains two spur gear and a test bearing while operating at a predetermined load with at least one copper catalyst strip blank inside the test gear box during the test.

6. The procedure of claim 1, wherein said testing the lubricant for thermal oxidation stability is accomplished by maintaining the heated test gear box at about 325° F.

7. The procedure of claim 1, wherein said testing the lubricant for thermal oxidation stability is accomplished in a heated test gear box while bubbling air at the rate of about 0.3 gallons per hour through the lubricant.

8. The procedure of claim 1, wherein said testing the lubricant for thermal oxidation stability is accomplished by testing the lubricant in a heated test gear box for about 300 hours of continuous operation and thereafter analyzing the test results by checking general appearance and cleanliness, and amounts of color of carbonaceous deposits.

9. The procedure of claim 1, wherein said thermal oxidation stability testing is accomplished by analyzing the increase of the viscosity of the proposed lubricant used in the heated test gear box.

10. The procedure of claim 1, wherein said thermal oxidation stability testing is accomplished by evaluating the total acidity of the lubricant after the test.

11. The procedure of claim 1, wherein said testing the lubricant for corrosion resistance is accomplished by heating the copper strip blank immersed in the test lubricant to an elevated temperature of about 250° F.

12. The procedure of claim 11, wherein said heating is carried out for about 3 hours to effect the test.

13. The procedure of claim 1, wherein said field testing to evaluate the ability to withstand extended drain intervals is accomplished by doing the test on at least about 100 new, substantially identical vehicles each run in on-highway service for at least 275,000 miles without changing the lubricant, before inspecting the transmission parts.

14. The procedure of claim 1, further comprising testing for seal life by testing vehicles which have each been run in on-highway service for at least 300,000 miles without changing the lubricant.

15. The procedure of claim 14, wherein testing for seal life is accomplished by testing at least about 50 new, substantially identical vehicles which have been run in on-highway service for at least 300,000 miles without changing the lubricant and evaluating the appearance of the rear bearing covers and seals for general appearance, evidence of wearing or degradation of the seal or any mating surfaces, and for the amount and color of carbonaceous deposits existing as varnish and sludge on the rear bearing cover seal.

16. A procedure for qualifying a proposed synthetic gear lubricant to be used in transmissions having a rear bearing cover and a rear bearing cover seal, comprising:
    testing the lubricant for compatibility with previously approved synthetic lubricants;
    testing the lubricant for thermal oxidation stability by testing the lubricant in a heated test gear box;
    testing the lubricant for corrosion resistance by a copper strip tarnish test;
    field testing the proposed gear lubricant to evaluate the ability of the lubricant to withstand extended drain intervals while still performing as functioned; and
    testing for seal life by testing at least about 50 new, substantially identical vehicles which have each been run in on-highway service for at least 300,000 miles without changing the lubricant and evaluating the appearance of the rear bearing covers and seals for general appearance, evidence of wearing or degradation of the seal or any mating surfaces, and for the amount and color of carbonaceous deposits existing as varnish and sludge on the rear bearing cover seal.

17. The procedure of claim 16, wherein said testing for compatibility includes heating the proposed synthetic lubricant with an approved lubricant in varying combinations having weight percentage ratios of 90/10, 75/25, 50/50, 25/75, and 10/90.

18. The procedure of claim 16, wherein said heating is accomplished with each weight percentage ratio at 0° F., 70° F., and 150° F.

19. The procedure of claim 16, wherein said testing the lubricant for compatibility is accomplished by blending the proposed lubricant with the previously approved synthetic lubricants for about 30 days in order to evaluate for haze or separation.

20. The procedure of claim 16, wherein said testing for thermal oxidation stability by testing the lubricant in a heated test gear box is accomplished by using a heated test gear box which contains two spur gears and a test bearing while operating at a predetermined load with at least one copper catalyst strip blank inside the test gear box during the test.

21. The procedure of claim 16, wherein said testing the lubricant for thermal oxidation stability is accomplished by maintaining the heated gear box at about 325° F.

22. The procedure of claim 16, wherein said testing the lubricant for thermal oxidation stability is accomplished in a heated gear box while bubbling air at a rate of about 0.3 gallons per hour through the lubricant.

23. The procedure of claim 16, wherein said testing the lubricant for thermal oxidation stability is accomplished by testing the lubricant in a heated gear box for about 300 hours of continuous operation and thereafter analyzing the test results by checking general appearance and cleanliness, and amounts of color of carbonaceous deposits.

24. The procedure of claim 16, wherein said thermal oxidation stability testing is accomplished by analyzing the increase of the viscosity of the proposed lubricant used in the heated test gear box.

25. The procedure of claim 16, wherein said thermal oxidation stability testing is accomplished by evaluating the total acidity of the lubricant after the test.

26. The procedure of claim 16, wherein said testing the lubricant for corrosion resistance is accomplished by heating the copper strip blank immersed in the test lubricant to an elevated temperature of about 250° F.

27. The procedure of claim 16, wherein said testing the lubricant in a heated test gear box is accomplished by heating for about 3 hours to effect the test.

28. The procedure of claim 16, wherein said field testing to evaluate the ability to withstand extended drain intervals is accomplished by doing the test on at least about 100 new, substantially identical vehicles each run in on-highway service for at least 275,000 miles without changing the lubricant, before inspecting the transmission parts.

29. A procedure for qualifying a proposed synthetic gear lubricant to be used in a transmission having an internal case, a shift bar housing, internal case rear seals, rear bearing covers and rear bearing cover seals, comprising:

(a) compatibility testing the proposed lubricant by heating the proposed synthetic lubricant with an approved lubricant in weight percentage ratios of 90/10, 75/25, 50/50, 25/75, and 10/90, respectively, at 0° F., 70° F., and 150° F., respectively, for about 30 days to evaluate for haze or separation;

(b) stability testing the proposed lubricant for thermal oxidation by testing the lubricant in a heated test gear box containing two spur gears and a test bearing while operating at a predetermined load with at least one copper catalyst strip inside the test gear box, maintaining the test gear box at about 325° F. while bubbling air at the rate of about 0.3 gallons per hour through the lubricant for about 300 hours of continuous operation, and thereafter analyzing the test results by checking general appearance and cleanliness, assessing resultant carbonaceous deposits of sludge and varnish including on the gears for color, analyzing the increase of the viscosity of the lubricant, and evaluating the total acid number in the lubricant after the test;

(c) corrosion testing the proposed lubricant by a copper strip tarnish test including placing a copper strip blank into a test bomb containing the lubricant to be tested, heating the test bomb to elevate the temperature to about 250° C. for about three hours with a showing of slightly tarnished light orange surface on the copper strip blank after the test;

(d) field testing the proposed lubricant to evaluate the ability of the lubricant to withstand extended drain intervals while still performing its function, said field testing being done in at least about 100 new, substantially identical vehicles in on-highway service for at least 275,000 miles each, without changing the lubricant, by inspecting the transmission after on-highway service, including the internal transmission case, the shift bar housing, the internal case rear seals, and other transmission parts for wear and to evaluate the appearance for cleanliness as well as an evaluation of the amount and color of carbonaceous deposits existing as varnish and sludge within the transmission; and (e) seal like testing by evaluating the appearance of the rear bearing covers and seals in at least about 50 new, substantially identical vehicles which have each been run in on-highway service for at least 300,000 miles without changing the proposed synthetic gear lubricant for general appearance, evidence of wearing or degradation of the seals or any mating surfaces, and the amount and color of carbonaceous deposits existing as varnish and sludge on the rear bearing cover seal.

* * * * *